United States Patent [19]

Gosselink et al.

[11] 4,159,277
[45] Jun. 26, 1979

[54] ZWITTERIONIC COMPOUNDS WITH A TETRAMETHYLENE OXIDE MOIETY BETWEEN THE CATIONIC AND ANIONIC CHARGE CENTERS

[75] Inventors: Eugene P. Gosselink, Cincinnati; James M. Richmond, Fairfield, both of Ohio

[73] Assignee: The Procter & Gamble Company, Cincinnati, Ohio

[21] Appl. No.: 770,489

[22] Filed: Feb. 22, 1977

Related U.S. Application Data

[63] Continuation of Ser. No. 562,307, Apr. 2, 1975, abandoned.

[51] Int. Cl.² ............ C07C 141/02; C11D 1/18
[52] U.S. Cl. ............ 260/458 R; 260/458 C; 260/501.12; 260/502.4 R; 252/526; 252/545; 252/546
[58] Field of Search ............ 260/501.12, 458, 458 R, 260/458 C

[56] References Cited

U.S. PATENT DOCUMENTS

| | | | |
|---|---|---|---|
| 3,452,066 | 6/1969 | Mannheimer | 260/401 |
| 3,684,427 | 8/1972 | Walz et al. | 260/501.12 X |
| 3,925,262 | 12/1975 | Laughlin et al. | 260/501.12 |
| 3,929,678 | 12/1975 | Laughlin et al. | 260/501.12 |

FOREIGN PATENT DOCUMENTS 813502  10/1974  Belgium ................ 260/458

*Primary Examiner*—James O. Thomas, Jr.
*Assistant Examiner*—G. T. Breitenstein
*Attorney, Agent, or Firm*—Robert B. Aylor; Richard C. Witte; Thomas H. O'Flaherty

[57] ABSTRACT

Surfactant compounds of the formula

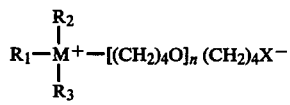

wherein $R_1$, $R_2$ and $R_3$ are, for example, straight chain, branched chain, or cyclic alkyl, alkenyl, aryl or alkaryl moieties, or wherein two R groups are joined in a ring structure; M is nitrogen or phosphorus; X is an anionic moiety such as sulfate or sulfonate; and n is an integer of from about 1 to about 20, are useful detergents.

15 Claims, No Drawings

ZWITTERIONIC COMPOUNDS WITH A TETRAMETHYLENE OXIDE MOIETY BETWEEN THE CATIONIC AND ANIONIC CHARGE CENTERS

This is a continuation of application Ser. No. 562,307, filed Apr. 2, 1975, now abandoned.

BACKGROUND OF THE INVENTION

This invention relates to tetramethylene oxide (TMO) compounds which exhibit superior clay and oily soil removal even in very low-built detergent systems. More particularly, this invention encompasses zwitterionic compounds characterized by a particular placement and number of TMO groups and particular hydrophobic groups. Importantly, the TMO moiety can be introduced into the instant compounds using tetrahydrofuran as a precursor. Tetrahydrofuran, in turn, is available from plant by-products such as corncobs, oat hulls, cottonseed hulls, and bagasse. To this extent, the instant compounds are not based on scarce petrochemical feedstocks in the manner of ethylene oxide-containing detersive surfactants.

Zwitterionic compounds, i.e., the so-called "internally neutralized" surface active compounds having both positive and negative charge centers, are known. In contrast with many prior art zwitterionics, the instant invention encompasses zwitterionic compounds having a substituent which provides both charge separation and hydration interposed between the oppositely-charged centers of the molecule.

Various zwitterionic compounds are known, and attempts have been made to tailor these compounds to provide detersive surfactants.

U.S. Pat. No. 3,684,427, to Walz, et al., issued Aug. 15, 1972, discloses alkoxylated zwitterionic surfactants and their use in fabric dyeing operations.

Belgian Pat. No. 813,502, to GAF Corporation, relates to di-ethoxylated quaternary ammonium compounds, phosphated or sulfated to form amphoteric surfactants. The compounds contain two alkylene oxide chains. U.S. Pat. No. 3,505,396, to H. L. Sanders, et al., issued Apr. 7, 1970, relates to sulfopropylated amphoteric surfactants containing ethylene oxide chains. U.S. Pat. No. 3,673,158, to A. M. Reader, et al., issued June 27, 1972, relates to sulfobetaine glycol modified with poly(ethylene terephthalate). U.S. Pat. No. 3,239,560, to C. M. Cambre, et al., issued Mar. 8, 1966, relates to the preparation of sulfobetaines having a hydroxy-substituted alkylene moiety interposed between the positive and negative charge centers of the surfactant-type molecules. U.S. Pat. No. 2,185,163, to H. Ulrich, issued Dec. 26, 1939, relates to alkoxylated derivatives of amine oxides containing anionic substituents. U.S. Pat. No. 2,115,250, to H. A. Bruson, issued Apr. 26, 1938, relates to alkoxylated amines and their salts and to the quanternary ammonium bases and salts derived from said amines. British Patent Specification No. 465,200, complete specification accepted April 26, 1937, relates to quaternary ammonium or phosphonium, or tertiary sulfonium, compounds containing ether or polyether groups.

The co-pending application of Laughlin, Gosselink, Cilley, and Heuring, Ser. No. 493,951, filed Aug. 1, 1974, now abandoned, relates to zwitterionic surfactants having ethylene oxide moieties interposed between the cationic and anionic charge centers. The co-pending application of Laughlin, Gosselink, and Cilley, Ser. No. 493,956, filed Aug. 1, 1974, now abandoned, relates to di-ethoxylated zwitterionic compounds having ethylene oxide groups interposed between the charge centers.

U.S. Pat. Nos. 3,668,240, issued June 5, 1972 and 3,764,568, issued Oct. 9, 1973, both to Barbera, disclose zwitterionic detergents having a 1,4-(2-butenylene) moiety between charge centers. U.S. Pat. Nos. 3,452,066, issued June 24, 1969, and 2,781,390, issued Feb. 12, 1957, both to Mannheimer, broadly relate to various zwitterionic surfactants optionally containing a seemingly limitless variety of oxygen-containing, presumably hydrophilic, moieties, including alkylene oxides. U.S. Pat. No. 3,769,311, issued Oct. 30, 1973, to Armstrong and Dawald, discloses ethoxylated ammonio carboxylate zwitterionics, and describes compounds having limited ranges of ethyleneoxy and hydrophobic groups attached to the positive charge center. Also, Belgium Arrete No. 806,567 issued Oct. 29, 1973 to Recket and Colman Products, Ltd., discloses anionic ethoxylated amino sulfonates. (See also Japanese 3555 (1962), to Komori and Kashiwabara, Chem Abstracts 53:4756e; British Pat. No. 1,296,351, complete Specification published Nov. 15, 1972, to Cheng et al.; U.S. Pat. No. 3,178,366, issued Apr. 13, 1965 to Du Brow and Brandiff; U.S. Pat. No. 2,940,816, issued June 14, 1960 to Sniegowski; and German Application No. 1,159,957, filed Nov. 8, 1960 by Glabisch, et al., for other zwitterionic and/or quaternary ammonium compounds.)

While a variety of surfactant classes are known, i.e., nonionic, anionic, cationic and zwitterionic, few of the usual types of detersive surfactants provide the advantageous performance of the instant compounds. The shortcomings of the art-recognized surfactants are well-known, and such materials must be built and/or otherwise precisely formulated to provide good soil removal under a variety of conditions. Moreover, it is common practice to blend various types of surfactants with builders to achieve both particulate and oily soil removal, since few, if any, surfactants are highly effective for removing both types of soil. Remarkably, the compounds herein exhibit detergency performance which approaches or exceeds many fully formulated and built detergent compositions in present commercial use, even without the use of builders, surfactant blends, or additives.

The instant invention is based on the discovery that the TMO moiety, properly interposed between the charge centers of zwitterionic surfactants having particular hydrophobic groups, provides compounds which exhibit unexpectedly high particulate soil removal performance in unbuilt laundry baths. Moreover, the compounds of this type are effective for removing oily soil.

The importance of the present invention is readily seen. A variety of surfactant types are known to remove soils, but none effectively remove both oily an particulate soil. Moreover, commercial detergent compositions are usually formulated with inorganic builders to remove a variety of soils under a variety of conditions. While such compositions are effective, the use of high concentrations of inorganic builders has raised questions regarding their presence in improperly treated sewage effluents. While organic builders are effective, they are expensive, especially when considering the substantial amounts used in common laundry situations.

The importance of the present invention is further seen when considering that other zwitterionic compounds having smaller, less extensively hydratable moieties (e.g., 2-hydroxy-1,3-propylene) separating the charge centers require builders and/or electrolytes to provide solubility and good cool water detergency (see, for example, U.S. Pat. No. 3,619,115, issued Nov. 9, 1971, to Diehl and Smith). The high water solubility of the preferred compounds herein eliminates the need for solubilizing additives such as builders or other electrolytes.

Finally, as noted above, the TMO-based compounds herein are prepared using tetrahydrofuran, rather than ethylene oxide, as a primary feedstock. The current and projected cost and availability of petrochemicals makes this an important consideration to detergent manufacturers. It is to be recognized that the zwitterionic surfactants herein are excellent emulsifiers and suspending agents, and are useful in a variety of compositions other than for their detergency function. For example, the compounds herein are useful spreading aids for use with herbicides and insecticides. The compounds are also useful as oil recovery aids, ore flotation aids, and the like.

It is an object of the present invention to provide zwitterionic detergent compounds which remove both particulate and oily soil from flexible substrates such as fabrics, as well as from hard surfaces such as walls and floors.

It is another object herein to provide zwitterionic compounds which can be used to cleanse both fabrics and hard surfaces without the need for builders or additives.

It is another object to prepare detersive surfactants using tetrahydrofuran as a feedstock.

These and other objects are obtained herein as will be seen from the following disclosures.

SUMMARY OF THE INVENTION

This invention encompasses zwitterionic surfactant compounds of the formula

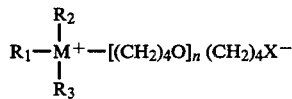

wherein $R_1$, $R_2$, $R_3$, M, X and n are as defined below.

DETAILED DESCRIPTION OF THE INVENTION

In its broadest aspect, the present invention encompasses zwitterionic compounds comprising molecules made up of four distinct parts. Referring to the foregoing formula, the compounds herein comprise a hydrocarbon portion composed of groups $R_1$, $R_2$ and $R_3$, a cationic charge center, M, an anionic charge center, X, and a tetramethylene oxide moiety interposed between said cationic and anionic charge centers.

The hydrocarbon portion of the present compounds can comprise straight, branched chain, etc., alkyl or alkenyl moieties, or aryl or alkaryl moieties, all as more fully described hereinafter. It will be understood by those skilled in the detergency arts that the hydrocarbon groups $R_1$, $R_2$ and $R_3$ can contain other substituents, such as halogen, hydroxyl, alkoxyl, and the like.

The cationic charge center in the present compounds is ammonium or phosphonium, with ammonium being preferred due to the availability of amine precursor compounds.

The anionic charge center, X, can be, for example sulfonate, sulfate, phosphonate, and like negatively charged moieties well recognized in the detergency arts as useful for imparting water solubility to detersive surfactants. Compounds of the present type wherein X is sulfate or sulfonate are highly preferred from the standpoint of ease-of-manufacture and detergency performance.

The present compounds are characterized by one or more TMO moieties interposed between the cationic and anionic charge centers of the molecule. The degree of polymerization of the TMO moieties is designated in the formula by integer n, which, in general, is within the range from about 1 to about 20, preferably from about 1 to about 10.

More particularly, hydrocarbon groups $R_1$, $R_2$ and $R_3$ can be independently selected from $C_1$-$C_{30}$ alkyl or alkenyl moieties; aryl moieties, such as phenyl, naphthyl, and the like; alkaryl moieties having an alkyl group in the range of $C_1$ to about $C_{30}$; or two R groups can be joined to form a $C_4$-$C_6$ heteroring compound with M.

When preparing a detersive surfactant of the present type, it will be recognized that groups $R_1$, $R_2$ and $R_3$ should be selected to provide sufficient hydrocarbon content that the hydrocarbon portion of the molecule has substantial hydrophobic character. More particularly, groups $R_1$ + $R_2$ + $R_3$ should, together, contain at least about 12 carbon atoms, more preferably at least about 14 carbon atoms.

Based on the foregoing considerations regarding the total hydrocarbon content of the groups $R_1$ + $R_2$ + $R_3$, it will be recognized by those skilled in the detergency arts that the hydrophobic character for good detergency performance is secured when, for example, goup $R_1$ is a straight chain or branched chain $C_{10}$-$C_{30}$ alkyl or alkenyl moiety, or an alkaryl moiety having a $c_6$-$C_{24}$ alkyl group, and $R_2$ and $R_3$ are each independently selected from $C_1$-$C_4$ alkyl or alkenyl moieties. Compounds wherein groups $R_1$ and $R_2$ are each independently selected from $C_6$-$C_{21}$ alkyl or alkenyl moieties and alkaryl moieties having a $C_6$-$C_{15}$ alkyl group, and wherein $R_3$ is a $C_1$-$C_4$ alkyl or alkenyl moiety, also have sufficient hydrocarbon content that the molecule has substantial hydrophobic character; accordingly, these are also highly useful detersive surfactants. Compounds wherein $R_1$, $R_2$ and $R_3$ are each independently selected from $C_6$-$C_{16}$ alkyl or alkenyl moieties and alkaryl moieties having a $C_6$-$C_{10}$ alkyl group are also useful detersive surfactants.

Typical detersive surfactants herein include the zwitterionic compounds wherein $R_1$ is a straight chain or a branched chain $C_{10}$-$C_{30}$ alkyl or alkenyl moiety, or an alkaryl moiety having a $C_6$-$C_{24}$ alkyl group (preferably $R_1$ is a $C_{14}$-$C_{22}$ alkyl moiety or alkaryl moiety having a $C_8$-$C_{16}$ alkyl group; more preferably $R_1$ is a $C_{14}$-$C_{20}$ alkyl moiety); $R_2$ and $R_3$ are each independently selected from $C_1$-$C_4$ alkyl or alkenyl moieties or hydroxy-substituted $C_1$-$C_4$ alkyl or alkenyl moieties (preferably $R_2$ and $R_3$ are each independently selected from $C_1$-$C_3$ alkyl moieties, especially methyl); X is sulfate or sulfonate; and n is an integer of at least 1 (preferably n is an integer from about 1 to about 10).

Other detersive surfactants are those wherein $R_1$ and $R_2$ are each independently selected from $C_6$-$C_{22}$ alkyl or alkenyl moieties and alkaryl moieties having a $C_6$-$C_{16}$ alkyl group (preferably $R_1$ and $R_2$ are each independently selected from $C_8$–$C_{16}$ alkyl moieties, most preferably $C_{10}$–$C_{14}$ alkyl moieties); $R_3$ is a $C_1$–$C_4$ alkyl or alkenyl, or $C_1$–$C_4$ hydroxy-substituted alkyl or alkenyl moiety (preferably $R_3$ is $C_1$–$C_3$ alkyl, especially methyl) the sum of $R_1 + R_2 + R_3$ carbon atoms being in the range from about 13 to about 50 (preferably in the range from about 14 to about 40); and wherein X and integer, n, are as defined immediately hereinabove.

Other representative detersive surfactants of the present type are those wherein groups $R_1$, $R_2$ and $R_3$ are each independently selected from $C_6$–$C_{16}$ alkyl or alkenyl moieties and alkaryl moieties having a $C_6$–$C_{10}$ alkyl group (preferably $R_1$, $R_2$ and $R_3$ are each independently selected from $C_8$–$C_{16}$ alkyl moieties, more preferably $C_8$–$C_{12}$ alkyl) the sum of $R_1 + R_2 + R_3$ carbon atoms being in the range from about 18 to about 48 (preferably about 24 to about 36); and wherein X and integer, n, are as defined immediately hereinabove.

The synthesis of the instant compounds is carried out using commercially available starting materials. A non-limiting example of one such synthetic route is as follows.

According to procedures described in the literature, tetrahydrofuran is refluxed with thionyl chloride and sulfuric acid for ca. 72 hours. The resulting products are represented by the dichloride (where x is 1 or 2).

Cl $(CH_2CH_2CH_2CH_2O)_x$ $CH_2CH_2CH_2CH_2Cl$     (I)

Sodium hydride is reacted with 1,4-tetramethylene glycol (excess, as solvent) until hydrogen evolution ceases. Dichloride (I) (x = 1) is then added to provide, for example

HO[$(CH_2)_4O]_4$H     (II)

Glycol (II) is thereafter tosylated in standard fashion with tosyl chloride in the presence of pyridine to form the ditosylate, represented by

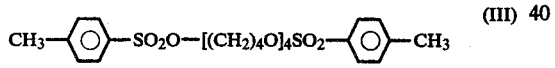

(III)

i.e., the TMO ditosylate.

The ditosylate (III) is then reacted with a tertiary amine (or phosphine) of the structure

(IV)

wherein $R_1$, $R_2$, $R_3$ and M are as defined above. The reaction of (III) with (IV) is conveniently carried out neat, or with a suitable solvent as N,N-dimethyl formamide or $CH_3CN$ at temperatures of 80° C. to about 100° C. to produce

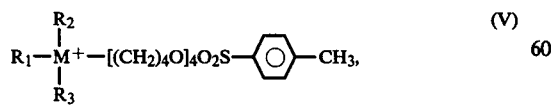

(V)

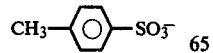

Reaction product (V) is then dissolved in aqueous methanol containing sodium sulfite and refluxed from 20–40 hours. The unreacted (V) and other ionic materials are removed by contacting the above solution with a mixed bed ion exchange resin (in the $H^+$, $OH^-$ form), followed by filtration of the solution and evaporation of the solvent to give, as the predominant zwitterionic product,

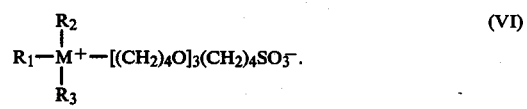

(VI)

It will be appreciated that zwitterionic compounds of the general formula (VI) can be prepared using any of a variety of tertiary amines or phosphines (IV). Moreover, zwitterionic compounds having any desired degree of polymerization of the TMO moiety (n) can be prepared in the same general fashion.

The following illustrates the preparation of the instant compounds, but is not intended to be limiting thereof. Precursors and products set forth in the examples include, inter alia, the following, wherein the letter designation corresponds to that used in the experimental procedure.

1,9-dichloro-5-oxanonane (A)

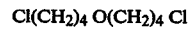

Cl$(CH_2)_4$ O$(CH_2)_4$ Cl 1,14-dichloro-5,10-dioxatetradecane (B)

Cl$(CH_2)_4$ O$(CH_2)_4$ O$(CH_2)_4$ Cl 1,19-dihydroxy-5,10,15-trioxanonadecane (C)

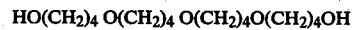

HO$(CH_2)_4$ O$(CH_2)_4$ O$(CH_2)_4$OH 1,24-dihydroxy-5,10,15,20-tetraoxatetracosane (D)

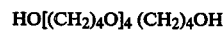

HO[$(CH_2)_4O]_4$ $(CH_2)_4$OH 1,19-(5,10,15-trioxanonadecylene)-bis(p-toluenesulfonate) (E)

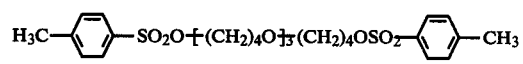

1,24-(5,10,15,20-tetraoxatetracosylene)-bis(p-toluenesulfonate) (F)

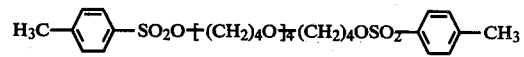

9-dimethyloctadecylammonio-5-oxanonane-1-sulfonate (G)

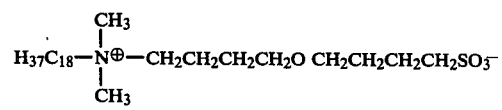

19-dimethyloctadecylammonio-5,10,15-trioxanonadecane-1-sulfonate (H)

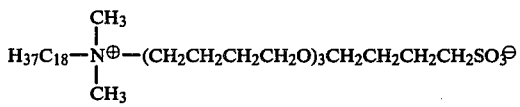

24-dimethyloctadecylammonio-5,10,15,20-tetraoxatetracosane-1-sulfonate (I)

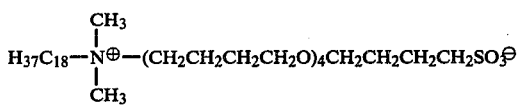

The following procedures relate to the synthesis of glycol and tosylated precursors used in the preparation of the instant compounds.

Preparation of 1,9-Dichloro-5-oxanonane (A) and 1,14-Dichloro-5,10-dioxatetradecane (B).

According to the chemistry of Reppe and Mitarbeiter, Ann 596, 38(1955), 15 g. of 95% sulfuric acid and 1 Kg. (13.9 mol) of thionyl chloride were added to 1.15 Kg. (16 mol) of dry tetrahydrofuran. This mixture was heated to reflux for 72 hrs; about 650 ml. of low boiling material (<70° C.) was then distilled and the residue fractionally distilled at low pressure. The first high boiling fraction gave 524 g. (2.6 mol) of title compound (A) (72° C./0.25 torr) and the second gave 212 g. (0.78 mol) of title compound (B) (145° C./0.6 torr).

Preparation of 1,19-Dihydroxy-5,10,15-Trioxanonadecane (C).

To 675 g. (7.5 mol) of 1,4-butanediol in a 3-neck, 2-l flask fitted with a mechanical stirrer, thermometer, and argon inlet valve was added 46 g. (2.0 g-atoms) of freshly cut sodium. After stirring under argon at room temperature for 16 hrs. the temperature was raised to 80° C. until the sodium had been consumed and hydrogen gas evolution had ceased. Two hundred thirty grams (1.15 mol) of dichloride (A) was then added dropwise over a four-hour period under argon, with stirring, and with the temperature at 80° C. This mixture was stirred under argon at 80° C. for an additional 20 hrs. and until the reaction mixture was neutral to litmus. The mixture was cooled, the precipitated sodium chloride filtered and washed with ethanol, and the filtrate distilled from solid potassium carbonate that was added to the distillation pot. After removal of low boiling material, four fractions were obtained: 204 g. (2.26 mol) of 1,4-butanediol (88° C./0.6 torr), 24.6 g. (150° C./2.0 torr) of uninvestigated material, 10.6 g. (180° C./2.0 torr) of uninvestigated material, and 50.0 g. (197°-230° C./2.0 torr) of title compound (C), m.p. 22° C.

Preparation of 1,24-dihydroxy-5,10,15,20-tetraoxatetracosane (D).

To 575 g. (6.4 mol) of 1,4-butanediol in a 2-l, 3-neck flask fitted with a mechanical stirrer, thermometer, and argon inlet valve was added slowly 61.5 g. (1.28 mol) of hexane rinsed sodium hydride (50% in mineral oil). After hydrogen evolution had ceased, the reaction temperature was raised to 80° C. and 173 g. (0.64 mol) of dichloride (B) was added dropwise. The mixture was stirred under argon at 80° C. for 17 hrs. and for an additional 50 hrs. at 130°-140° C. The mixture was then cooled, the precipitated sodium chloride filtered and washed with ethanol, and the filtrate distilled at reduced pressure. After distillation of some low boiling material, 447 g. (495 mol) of 1,4-butanediol (88° C./0.6 torr) was distilled. The pot residue was crystallized from ether. Thin layer chromatography indicated an impurity was present. Continuous extraction of the liquid melt with hexanes for 3 days removed the impurity. Crystallization from a seeded ethereal solution afforded pure title compound (D), 179 g., m.p. 34.5°-36.5° C.

Preparation of 1,19-(5,10,15-Trioxanonadecylene)-bis(p-Toluenesulfonate) (E).

To 61 g. (0.20 mol) of glycol (C) in 250 ml. (3.17 mol) of dry pyridine cooled to 0°-4° C. was added in small portions 84 g. (0.44 mol) of tosyl chloride (i.e., p-toluene sulfonyl chloride). Addition of tosyl chloride, with stirring, was controlled so that the reaction temperature remained below 8° C. After stirring for 3 hrs. at 5° C., the reaction mixture was poured into a slurry of 1 liter of 12 N hydrochloric acid and 3 liters of ice. This mixture was extracted with three 500 ml-portions of chloroform. The combined extracts were washed with water, saturated sodium bicarbonate solution, dried (Na$_2$SO$_4$), and the solvent removed to yield the title ditosylate (E), 121 g., as a viscous oil.

Preparation of 1,24-(5,10,15,20-Tetraoxatetracosylene)-bis(p-Toluenesulfonate) (F).

Forty grams (0.11 mol) of glycol (D) and 45 g. (0.23 mol) of tosyl chloride in 250 ml. (3.17 mol) of dry pyridine were allowed to react as in the preparation of E above. Evaporation of the solvent from the dried extract afforded 73 g. of product ditosylate (F) as a viscous oil.

EXAMPLE I

Preparation of 9-Dimethyloctadecylammonio-5-oxanonane-1-sulfonate (G)

Twenty-five grams (0.126 mol) of dichloride (A) and 37 g. (0.126 mol) of distilled (b.p. 176°-179° C.) dimethyloctadecylamine were heated at reflux in 150 ml of dry acetonitrile, with stirring, for 16 hrs. The solvent was then removed and the residue dissolved in 500 ml. of water. Fifty grams (0.40 mol) of sodium sulfite were added and the reaction mixture was refluxed until all dichloride (A) had been consumed as determined by thin layer chromatography. The mixture was then cooled, and extracted with three 200 ml-portions of chloroform. The combined extracts were dried (Na$_2$SO$_4$), the solvent evaporated, and the residue dissolved in methanol.

The above methanol solution was stirred with 400 g. of a mixed bed ion exchange resin (Rexyn ® 300 H-OH, commercially available from the Fisher Scientific Company) for 5 hrs. The resin was then filtered and the methanol solution concentrated to yield 19 g. of title compound (G) m.p. 114°-116° C.

The procedure of Example I is modified by replacing the C$_{18}$H$_{37}$(CH$_3$)$_2$N with an equivalent amount of n-

$C_{10}H_{21}(CH_3)_2N$, n-$C_{12}H_{25}(CH_3)_2N$, n-$C_{14}H_{29}(CH_3)_2N$, n-$C_{16}H_{33}(CH_3)_2N$ and n-$C_{20}H_{41}(CH_3)_2N$, respectively, and the corresponding dimethylammonio compounds wherein $R_1$ is, respectively, n-$C_{10}$; n-$C_{12}$; n-$C_{14}$; n-$C_{16}$; and n-$C_{20}$ are secured.

EXAMPLE II

Preparation of 19-Dimethyloctadecylammonio-5,10,15-trioxanonadecane-1-sulfonate (H).

To 58 g. (0.096 mol) of ditosylate (E) in 150 ml. of dry acetonitrile was added 28 g. (0.096 mol) of distilled (b.p. 176°–179° C.) dimethyloctadecylamine. This mixture was heated to reflux under argon, with stirring, for 16 hrs. The solvent was then removed and the residue dissolved in 500 ml. of methanol. Thirty-six grams (0.29 mol) of sodium sulfite in 500 ml. of water were added to the methanolic solution and this mixture was heated to reflux until thin layer chromatography indicated the absence of ditosylate (E). Additonal methanol was added and the insoluble salts were filtered. The solvents were removed, the residue dissolved in methanol, and the methanolic solution purified with mixed bed resin as in Example I. Filtration of the resin and evaporation of the solvent afforded 15 g. of the title compound (H), m.p. 24° C.

In the foregoing procedure, the dimethyloctadecylamine is replaced by an equivalent amount of dimethyldodecylphosphine, didecylmethylphosphine and trioctylphosphine, respectively. The compounds wherein $R_1$ is dodecyl and $R_2$ and $R_3$ are each methyl; wherein $R_1$ and $R_2$ are each decyl and wherein $R_3$ is methyl; and wherein $R_1$, $R_2$ and $R_3$ are each octyl, are secured, respectively.

EXAMPLE III

Preparation of 24-Dimethyloctadecylammonio-5,10,15,20-tetraoxatetracosane-1-sulfonate (I).

Fifty grams (0.073 mol) of ditosylate (F) and 22 g. (0.073 mol) of distilled (b.p. 176°–179° C.) dimethyloctadecylamine were allowed to react as in the preparation of (H), above. After removal of the solvent, the residue was allowed to react with 27 g. (0.21 mol) of sodium sulfite in one liter of aqueous methanol (1:1, v/v) at reflux temperatures. After purification, as in the preparation of (H), above, the compound was crystallized from 1:1 ethyl acetate-chloroform and vacuum dried to yield 12 g. of the title compound (I), m.p. 61° C.

In the foregoing procedure, the dimethyloctadecylamine is replaced by an equivalent amount of dimethylbutyl amine and the corresponding sulfonate (wherein $R_1$ is butyl and $R_2$ and $R_3$ are each methyl) is secured.

In the foregoing procedure, the dimethyloctadecylamine is replaced by an equivalent amount of dioctylmethylamine and the corresponding sulfonate (wherein $R_1$ and $R_2$ are each octyl and $R_3$ is methyl) is secured.

In the foregoing procedure the dimethyloctadecylamine is replaced by an equivalent amount of $(C_{10}H_{21})_3N$ and the corresponding sulfonate (wherein $R_1$, $R_2$ and $R_3$ are each decyl) is secured.

EXAMPLE IV

Preparation of 19-Dimethyloctadecylammonio-5,10,15-Trioxanonadecane-1-Sulfate.

To 61 g (0.20 mol) of glycol (C) in 250 ml (3.17 mol) of dry pyridine cooled to 0.4° C. is added in small portions 38 g (0.20 mol) of tosyl chloride as in the preparation of E. Purification and removal of solvent as in the preparation of E affords a mixture of C, E, and the monotosylate of C. This mixture in 150 mls. of dry acetonitrile with 0.20 mol of dimethyloctadecylamine is heated to reflux in the manner of Example II, and the solvent stripped on a rotary evaporator.

The mixture of material prepared in the foregoing manner is dissolved in 250 mls. of dry pyridine and cooled to 0°–5° C. Chlorosulfonic acid, 56 g (0.48 mol), dissolved in 250 ml of chloroform, is added dropwise to maintain the reaction temperature below 15° C. After addition of the chlorosulfonic acid, the mixture is stirred at 0° C. for 1 hr., and at room temperature for an additional hour.

Following the reaction with the chlorosulfonic acid, the chloroform is vacuum-stripped. The semi-solid residue is poured into cooled 50% aqueous NaOH and extracted three times with chloroform. The combined extracts are purified with mixed bed resin (Rexyn ® 300 H-OH) to yield the title compound.

In the foregoing procedure, the n-$C_{18}H_{37}(CH_3)_2N$ is replaced by an equivalent amount of n-$C_{10}H_{21}(CH_3)_2N$, n-$C_{12}H_{25}(CH_3)_2N$, n-$C_{14}H_{29}(CH_3)_2N$, n-$C_{16}H_{33}(CH_3)_2N$, n-$C_{16}H_{31}(CH_3)_2N$, and n-$C_{20}H_{41}(CH_3)_2N$, respectively. The corresponding dimethylammonio sulfates wherein $R_1$ is decyl, dodecyl, tetradecyl, hexadecyl, hexadecnyl and eicosyl are secured, respectively.

In the foregoing procedure, the dimethyloctadecylamine is replaced by an equivalent amount of the following phosphines, respectively: dimethyldodecylphosphine; dimethyloctadecylphosphine; tris(decyl)phosphine; tritetradecylphosphine; and didodecylmethylphosphine. The corresponding phosphonium 5,10,15-trioxanonadecane sulfates are secured in each instance.

EXAMPLE V

Preparation of 24-Dimethyloctadecylammonio-5,10,15,20-Tetraoxatetracosane-1-hydrogen Phosphonate.

To 40 g (0.11 mol) of glycol (D) in 100 ml of dry dimethylformamide is added 62 g (0.30 mol) of thionyl bromide. This mixture is heated until the conversion of the glycol to the dibromo-compound is complete, and then neutralized with base. This neutralized mixture is extracted with chloroform, the extracts dried ($Na_2SO_4$), and the solvent removed to yield the dibromo-derivative of D.

The material prepared above is then heated not higher than 130° C. with 21 g (0.10 mol) of isopropylphosphite as 2-bromopropane distills. After the 2-bromopropane has all distilled, the reaction pressure is reduced to about 1 torr., whereupon additional low boiling distillates are removed.

The residue from the distillation above is cooled and chromatographed on silica gel to isolate the diisopropyl bromophosphonate. This purified monoester is allowed to react with an equal mole amount of dimethyloctadecylamine in refluxing acetonitrile in the manner of Example II, and the solvent removed. This quaternary ammonium phosphonate ester is hydrolyzed with 3-6 hydrochloric acid to yield, after purification and solvent removal, the title compound.

What is claimed is:

1. A compound of the formula:

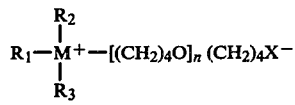

$$R_1-\overset{\overset{R_2}{|}}{M^+}-[(CH_2)_4O]_n(CH_2)_4X^-$$
$$\underset{R_3}{|}$$

wherein $R_1$, $R_2$ and $R_3$ are each straight chain or branched chain or cyclic alkyl, alkenyl or aryl or alkaryl moieties; M is nitrogen or phosphorus; n is an integer from 1 to about 20; and X is a water-solubilizing anionic moiety.

2. A compound according to claim 1 wherein $R_1$, $R_2$ and $R_3$ are independently selected from $C_1$–$C_{30}$ alkyl or alkenyl moieties, aryl moieties, alkaryl moieties having an alkyl group in the range of $C_1$–$C_{30}$.

3. A compound according to claim 1 wherein X is sulfate, sulfonate or phosphonate.

4. A detersive surfactant compound according to claim 3 wherein $R_1 + R_2 + R_3$, together, contain at least about 12 carbon atoms.

5. A detersive surfactant compound according to claim 4 wherein $R_1$ is a straight chain or branched chain $C_{10}$–$C_{30}$ alkyl or alkenyl moiety, or an alkaryl moiety having $C_6$–$C_{24}$ alkyl group, and wherein $R_2$ and $R_3$ are each independently selected from $C_1$–$C_4$ alkyl or alkenyl moieties or hydroxy-substituted $C_1$–$C_4$ alkyl or alkenyl moieties.

6. A detersive surfactant compound according to claim 5 wheren $R_1$ is a $C_{14}$–$C_{22}$ alkyl moiety or alkaryl moiety having a $C_8$–$C_{16}$ alkyl group, $R_2$ and $R_3$ are each methyl, X is sulfate or sulfonate, M is nitrogen, and n is an integer in the range from 1 to about 10.

7. A detersive surfactant compound according to claim 6 which is 9-dimethyloctadecylammonio-5-oxanonane-1-sulfonate.

8. A detersive surfactant compound according to claim 6 which is 19-dimethyloctadecylammonio-5,10,15-trioxanonadecane-1-sulfonate.

9. A detersive surfactant compound according to claim 6 which is 24-dimethyloctadecylammonio-5,10,15,20-tetraoxatetracosane-1-sulfonate.

10. A detersive surfactant compound according to claim 6 which is 19-dimethyloctadecylammonio-5,10,15-trioxanonadecane-1-sulfate.

11. A detersive surfactant compound according to claim 4 wherein $R_1$ and $R_2$ are each independently selected from $C_6$–$C_{22}$ alkyl or alkenyl moieties or alkaryl moieties having a $C_6$–$C_{16}$ alkyl group and wherein $R_3$ is a $C_1$–$C_4$ alkyl or alkenyl moiety or hydroxy-substituted $C_1$–$C_4$ alkyl or alkenyl moiety.

12. A detersive surfactant compound according to claim 11 wherein $R_1$ and $R_2$ are each selected from $C_8$–$C_{16}$ alkyl moieties, $R_3$ is methyl, X is sulfate or sulfonate, M is nitrogen, and n is an integer in the range from 1 to about 10.

13. A detersive surfactant compound according to claim 4 wherein $R_1$, $R_2$ and $R_3$ are each independently selected from $C_6$–$C_{16}$ alkyl or alkenyl moieties or alkaryl moieties having a $C_6$–$C_{10}$ alkyl group.

14. A detersive surfactant compound according to claim 13 wherein $R_1$, $R_2$ and $R_3$ are each independently selected from $C_8$–$C_{16}$ alkyl moieties, the sum of $R + R_2 + R_3$ carbon atoms being in the range from about 24 to about 48, X is sulfate or sulfonate, M is nitrogen, and n is an integer in the range from 1 to about 10.

15. A compound according to claim 1 which is 24-dimethyloctadecylammonio-5,10,15,20-tetraoxatetracosane-1-hydrogen phosphonate.

* * * * *

UNITED STATES PATENT AND TRADEMARK OFFICE
CERTIFICATE OF CORRECTION

PATENT NO. : 4,159,277
DATED : June 26, 1979
INVENTOR(S) : Eugene P. Gosselink and James M. Richmond It is certified that error appears in the above-identified patent and that said Letters Patent are hereby corrected as shown below:

Column 2, line 57, "an" should be -- and --.

Column 4, line 36, "goup" should be -- group --.

Column 4, line 38, "c$_6$" should be -- C$_6$ --.

Column 12, Claim 14, line 3, "R" should be -- R$_1$ --.

Signed and Sealed this

*Ninth* Day of *October 1979*

[SEAL]

*Attest:*

RUTH C. MASON
*Attesting Officer*

LUTRELLE F. PARKER
*Acting Commissioner of Patents and Trademark*